United States Patent
Stark et al.

(10) Patent No.: US 6,206,134 B1
(45) Date of Patent: Mar. 27, 2001

(54) COVER FOR STETHOSCOPE HEAD

(76) Inventors: Wayne T. Stark, 4787 Yorkshire Way, Granite Bay, CA (US) 95746; Raymond J. Mikelionis, 203 Grove St., Roseville, CA (US) 95678

( * ) Notice: Subject to any disclaimer, the term of this patent is extended or adjusted under 35 U.S.C. 154(b) by 0 days.

(21) Appl. No.: 08/812,049
(22) Filed: Mar. 8, 1997
(51) Int. Cl.[7] .................................................... A61B 7/02
(52) U.S. Cl. ................................................................ 181/131
(58) Field of Search ................................. 181/131, 137; 381/67; 128/715

(56) References Cited

U.S. PATENT DOCUMENTS

| | | | |
|---|---|---|---|
| 5,448,025 | * 9/1995 | Stark et al. | 181/131 |
| 5,587,561 | * 12/1996 | Budayr et al. | 181/131 |
| 5,686,706 | * 11/1997 | Wurzburger | 181/131 |

* cited by examiner

Primary Examiner—Khanh Dang
(74) Attorney, Agent, or Firm—Don Finkelstein

(57) ABSTRACT

A cover for a stethoscope head having a discontinuous layer of peelable adhesive in a predetermined pattern for detachable affixing to the head of the stethoscope including the diaphragm and the preselected pattern has a plurality of spaced apart adhesive segments and provides air flow passages from regions between the cover and the diaphragm to regions external the stethoscope to prevent the formation of air pockets and bubbles therebetween.

15 Claims, 2 Drawing Sheets

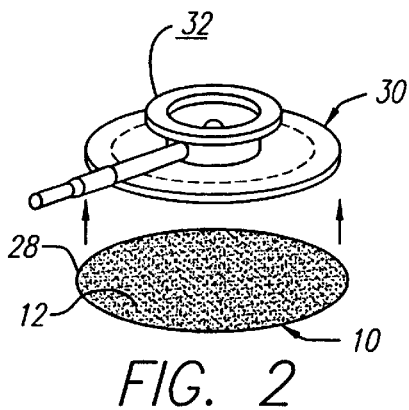
FIG. 2
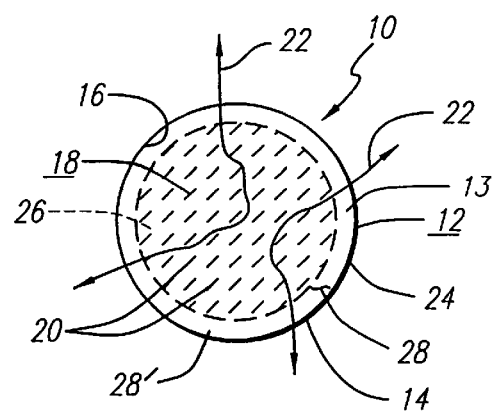
FIG. 1
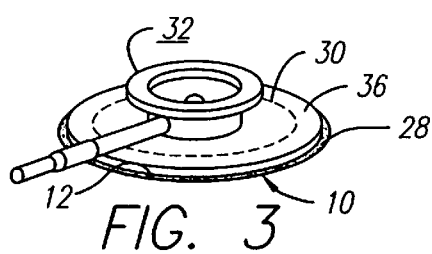
FIG. 3
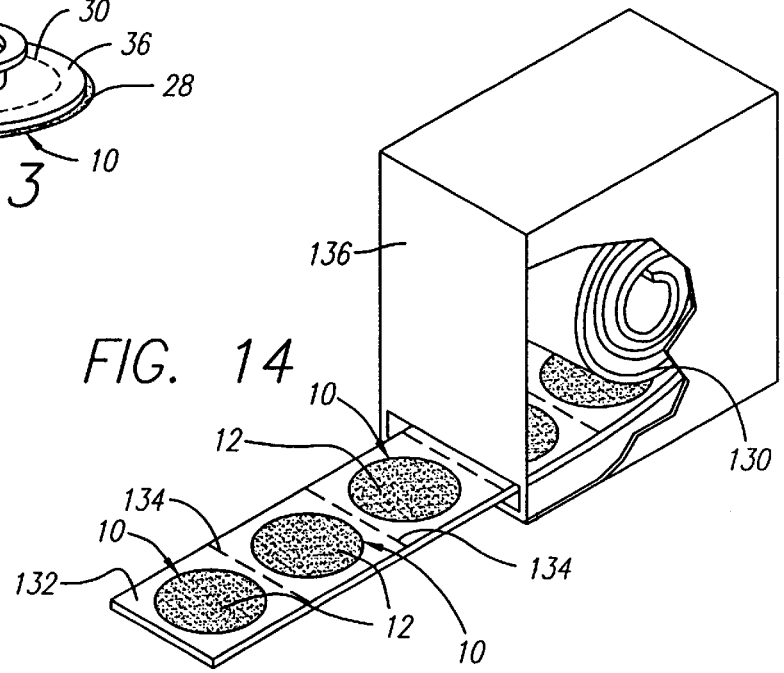
FIG. 14
FIG. 15
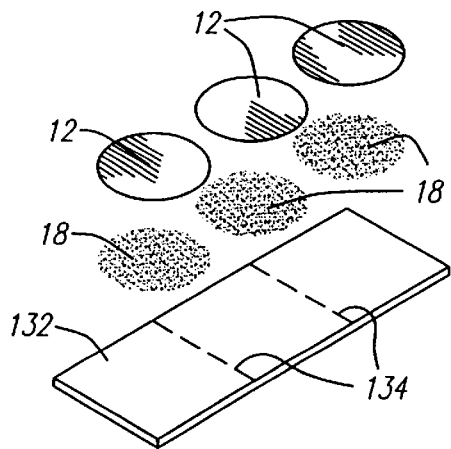
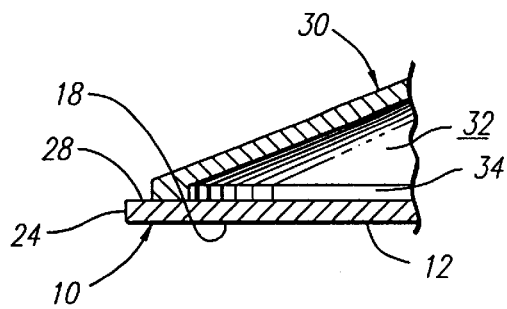
FIG. 4

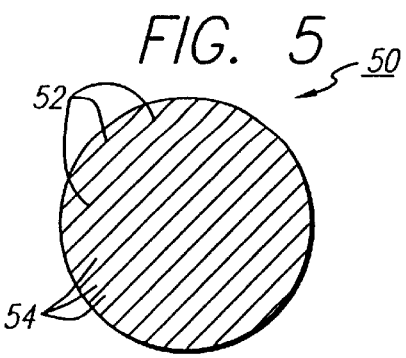
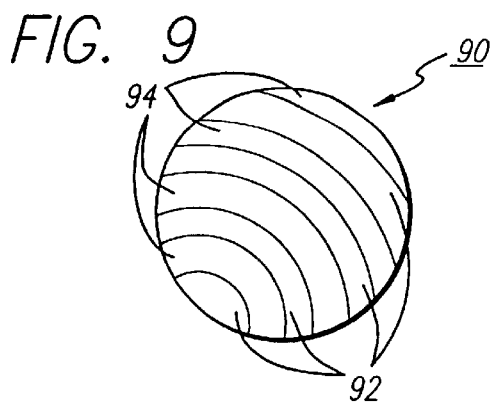
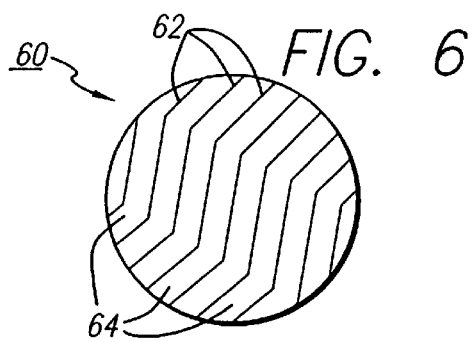
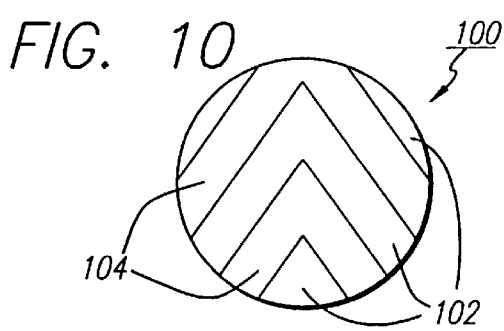
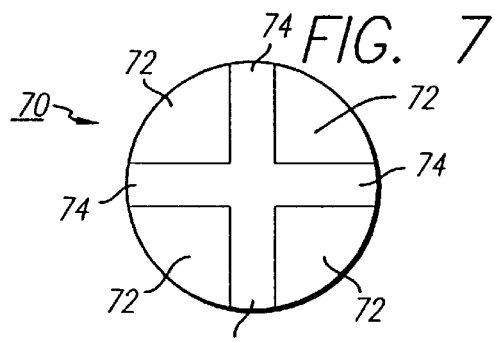
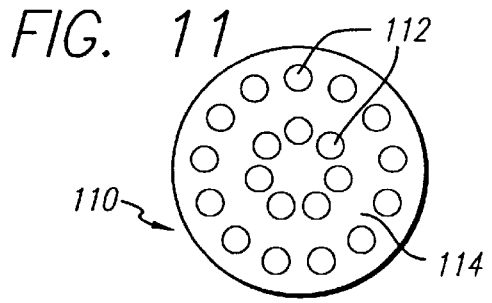
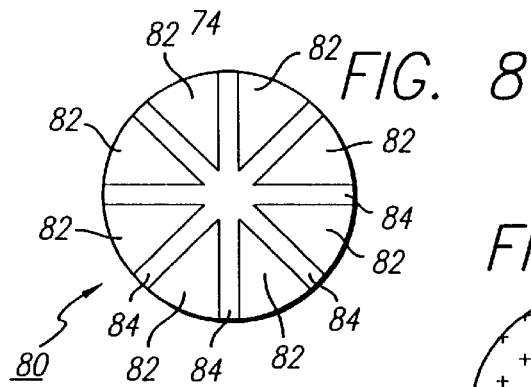
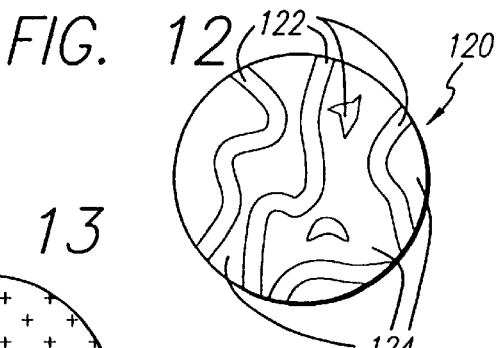
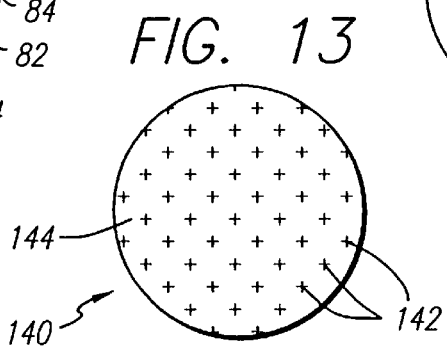

COVER FOR STETHOSCOPE HEAD

REFERENCE TO RELATED PATENT

This application is related to the invention in our U.S. Pat. No. 5,448,025 and the teaching and technology thereof are incorporated by reference herein.

BACKGROUND OF THE INVENTION

Field of the Invention

This invention relates to the medical devices art and more particularly to an improved detachable, disposable cover for a stethoscope head. The cover provides protection from patient to patient contamination and does not interfere with the intended purpose and function of the stethoscope.

Description of the Prior Art

A number of arrangements for providing protection to a stethoscope head have heretofore been proposed. Various patents show the range of covers and the different structures described therein for the purpose of covering the head of a stethoscope. In our U.S. Pat. No. 5,448,025 there is described a cover that is detachably secured by a peelable adhesive applied to one side of a thin plastic film to the head of the stethoscope to provide a seal thereover for protecting the stethoscope head from contamination from the ambient environment as well as preventing patient to patient contamination. Such an arrangement is satisfactory for many applications wherein the detection of comparatively strong sounds from the portion of the anatomy to which the stethoscope is applied is to be obtained.

In U.S. Pat. Nos. 5,424,495 and 5,528,004 there is described a disposable, detachable cover that is secured to the diaphragm of the stethoscope by an adhesive which is continuous over the entire surface of the cover in contact with the diaphragm.

Other United States patents have shown other variations of detachable covers for stethoscopes. In U.S. Pat. No. 4,871,046 there is described a disposable shield for a stethoscope head in the form of an envelope in which the sides of a thin plastic sheet are folded over defining two top portions overlying the bottom portion with heat sealed edges. This cover loosely covers the head of the stethoscope in the form of an envelope type covering with excess material above the head. Such excess material can move and thus distort the sound to be detected and interfere with the normal operation of the stethoscope in detecting the various bodily generated sounds. In U.S. Pat. No. 4,461,368 there is disclosed a comparatively complex and relatively expensive cover having a flexible latex membrane with a rigid rim. The use of the two separate parts of this cover can, in some situations, increase the likelihood of generating extraneous sounds which can mask or distort the sound it is desired to detect.

The state of the prior art is further indicated by the following U.S. Pat. Nos.: 5,054,063; 4,867,268; 4,867,265; 3,867,925; 3,614,991; 3,543,875; 3,225,841; 3,213,960; 2,651,380; 2,650,269; and 2,507,375.

In many applications, however, where the stethoscope is used to detect comparatively weak sounds or sounds that tend to be masked by other sounds, the prior art devices are not completely satisfactory. Not only must the cover be inexpensive so that it may be disposed after each use, but it must not distort or mask the sound to be detected. It has been found that in covers wherein a thin plastic film- like membrane is provided with an adhesive on one side thereof for detachably securing the cover to the diaphragm of the stethoscope some small air pockets may be trapped between the diaphragm and the cover. These trapped air pockets or air bubbles have been found to distort or mask the sounds which are to be detected. While manipulation of the cover on the diaphragm by repeated smoothing movements may eliminate some of the air pockets, such activity takes time and cannot guarantee removal of all trapped air pockets. Further, such manipulation of the cover on the diaphragm may damage the diaphragm.

It has been found that while complete sealing of the diaphragm head to eliminate possible environmental contamination is often desirable, the more important consideration is eliminating patient to patient contamination in order to achieve a lack of sound distorting or masking effects which could be caused by the cover. The protection from environmental contamination may be accomplished by any of the conventional techniques now used in the medical profession for such purposes. The stethoscope is, of course, exposed to the environment between applications of the cover. Therefore, the patient to patient type contamination can be prevented by the cover even in those structures where there is not complete protection from environmental contamination if the cover is designed to eliminate sound distortion or masking, or otherwise interfering with the intended purpose of the stethoscope.

Thus, there has long been a need for a cover for a stethoscope head that is inexpensive, quickly and easily attached, prevents or minimizes patient to patient contamination and which does not distort or mask the sounds it is desired to detect.

SUMMARY OF THE INVENTION

Accordingly, it is an object of the present invention to provide an improved stethoscope head cover that does not distort or mask the sounds to be detected.

It is another object of the present invention to provide a stethoscope head cover which minimizes or eliminates the possibility of patient to patient contamination and also eliminates the effect of sound distorting or masking caused by air pockets or bubbles trapped between the diaphragm and the cover.

It is yet another object of the present invention to provide such a stethoscope head cover that is inexpensive, can be quickly and easily installed and removed and may be conveniently dispensed to the user of the stethoscope.

The above, and other objects of the present invention are achieved, in a preferred embodiment of the present invention, by providing a stethoscope head cover which overlies the diaphragm of the stethoscope and the surrounding rim thereof and which is fabricated from a thin sheet of plastic with a discontinuous layer of peelable adhesive on one surface of the plastic. The discontinues layer of adhesive is in a predetermined pattern and the pattern is selected so that air passageways are provided from the regions between the cover and the diaphragm and past the rim to regions external the stethoscope. The cover generally comprises a flat, thin plastic sheet with the discontinuous layer of a peelable adhesive applied to one surface of the sheet. The adhesive adheres to both the diaphragm and the rim of the stethoscope leaving the aforesaid air passages for eliminating trapped air pockets or bubbles between the diaphragm and the cover. The preferred embodiments of the present invention utilize a thin sheet of vinyl as flat plastic sheet to form a membrane like body member with a uniform thickness in the broad range of from about 0.01 mil to about 1.0 mil. The preferred thickness range within this broad range is from about 0.1 mil to 0.4 mil. Since most stethoscope heads are round and the diaphragm therein is round, the preferred geometrical shape of the cover according to the present invention is also round with a diameter on the order of one half inch to three inches to accommodate the range of diaphragm sizes.

The pattern for the discontinuous layer of adhesive may be, for example, a plurality of small "dots" of adhesive of any desired geometric shape such as round, irregular, "T" shaped, + shaped or the like in a pattern of any desired spaced apart array over the surface of the plastic sheet. Other patterns for the discontinuous layer of adhesive may include a series of parallel stripes of adhesive, a series of zig-zag stripes of adhesive, a plurality of radial extending stripes of adhesive, a plurality of arcuate stripes of adhesive, or any other discontinuous layer of adhesive providing the desired air passageways.

BRIEF DESCRIPTION OF THE DRAWING

The above, and other embodiments of the present invention, may be more fully understood from the following detailed description taken together with the accompanying drawing wherein similar reference characters refer to similar elements and in which:

FIG. 1 is a plan view of a stethoscope head cover according to the principles of the present invention having a discontinuous layer of peelable adhesive comprised of small "dots" of adhesive in a random array;

FIG. 2 illustrates an exploded view of the cover shown in FIG. 1 about to be place on a stethoscope head;

FIG. 3 illustrates the cover of FIG. 1 in place on a stethoscope head;

FIG. 4 illustrates a partial sectional view of the cover installed on a stethoscope head;

FIGS. 5 through 12 illustrate various covers of the present invention having discontinuous adhesive layer patterns useful in the practice of the present invention;

FIG. 13 is a plan view of another embodiment of a cover of the present invention having a discontinuous layer of peelable adhesive comprised of small "+" shaped segments in a uniform rectilinear spaced apart array; and FIGS. 14 and 15 illustrate dispensing arrangements for the cover according to the principles of the present invention.

DESCRIPTION OF THE PREFERRED EMBODIMENTS

Referring now to the Drawing, there is shown in FIG. 1 thereof an embodiment 10 of a cover 12 according to the principles of the present invention. The cover 12 has as body member 13 which is a thin sheet of plastic having a thickness in the range of 0.01 mil to 1.0 mil and preferably in the range of 0.1 mil to 0.4 mil. The body member 13 has an upper surface 14 and a lower surface 16. The lower surface 16 is adapted to be placed upon and adhered to the structure in the head of a stethoscope which generally will comprise a diaphragm surrounded by a rigid rim. On the lower surface 16 there is provided a discontinuous layer of adhesive generally designated 18. The layer 18 is comprised of a plurality of spaced apart segments in a predetermined pattern. In FIG. 1 the adhesive is in the form of a plurality of segments which are spaced apart "dots" 20 of adhesive. The number of dots, the size of the dots and the space between the dots can vary depending upon the particular application. Further, the predetermined pattern of the dots 20 may be random or in some predetermined regular pattern. According to the principles of the present invention the pattern of the plurality of spaced apart segments of the adhesive is selected so that there are a plurality of air flow paths generally indicated by the arrows 22 from regions inside the outer peripheral edge 24 of the cover 12 to regions exterior the cover 12.

The dotted line 26 shown on the cover 12 indicates the extent of the outer diameter of the rim of the stethoscope head to which the cover 12 is to be applied as described below. Since most stethoscope heads are circular, the cover 12 of the present invention is also preferably circular and has a diameter in the range of one half inch to three inches to accommodate the various sizes of stethoscope heads. If desired, however, shapes other than circular may be selected for particular applications.

An annular border portion 28 may be provided on the cover 12 and the annular border portion 28 may be free of adhesive whether in the form of the dots 20 or in some other pattern, in its entirety, have an area as indicated at 28' free of adhesive with the remainder having the adhesive dots 20 or be completely covered by the adhesive dots 20 as may be desired for particular applications. The border portion 28 allows the convenient grasping of the cover 12 during the installation and removal of the cover 12 from a stethoscope head. The dots 20 allow detachable adhesion of the cover 12 to the diaphragm. The cover 12 provides protection against patient to patient contamination. The flow paths 28 allows air to be expelled from the interior of the cover 12 during the installation thereof so as to eliminate air pockets or bubbles between the cover 12 and the stethoscope and thus eliminate the sound distortion or masking effect of the air pockets. Even trace or faint sounds can be heard with a stethoscope to which the cover 12 is applied and even when there are other sounds present. Thus, the finer sounds such as rales (in the chest), rubs (in the heart), bruits, from blood vessels, (in the abdomen) may be heard with accurate sound fidelity to allow accurate diagnosis and appropriate treatment.

Referring now to FIGS. 2, 3 and 4 there is illustrated the installation of the cover 12 onto the head 30 of a stethoscope 32. The cover 12 is grasped by the border portion 28 and finger pressure is applied to the upper surface 14 of the cover 12 to press it on to the head 30 of the stethoscope 32. The adhesive layer 18 adheres to the diaphragm 34 of the stethoscope 32 and, if the adhesive layer 18 is present, also to the rim 36. The airflow passages 22 provided by the pattern of the adhesive layer 18, as shown in FIG. 1, allows any air that is present between the cover 12 and the diaphragm 34 to be expelled to regions external the stethoscope 32. The cover 12 moves with the diaphragm 36 during use of the stethoscope 32 and the absence of air pockets or bubbles allows true and accurate sound fidelity to be achieved.

FIGS. 5 through 12 illustrate various patterns of adhesive which are useful in the practice of the present invention. In the various embodiments, the pattern selected for the adhesive is such that there is always at least one air passage from regions interior of the cover 12 to regions exterior of the cover 12 so that air may pass therethrough during application of the cover to a stethoscope. Further, the larger the area of any one discrete element of adhesive on the cover 12, the greater is the chance that an air pocket will develop. If an air pocket does develop, the cover 12 so installed may be discarded and a new one applied, or finger pressure may be applied to upper surface 14 in a massaging type action to try and force any entrapped air into one of the air flow passages. In the embodiments shown in FIGS. 5 through 12, the adhesive layer in its pattern extends over the surface of the cover 12 including the border portions. However, in various applications, as noted above, the adhesive layer may be eliminated from all or part of the border.

In the embodiment 10 shown on FIG. 1, the dots 20 are in a random pattern and round in shape. The dots 20 could also be of irregular shape. In other variations of embodiment 10, the dots may be square, hexagonal or any other selected geometrical shape and may be in a regular or random space apart pattern.

FIG. 5 illustrates an embodiment 50 of the of the present invention in which the adhesive layer is in the pattern of a plurality of substantially parallel "lines" 52 leaving airflow passages 54 therebetween.

FIG. 6 illustrates an embodiment 60 of the of the present invention in which the adhesive layer is in the pattern of a plurality of substantially parallel "zig-zag lines" 62 leaving airflow passages 64 therebetween.

FIG. 7 illustrates an embodiment 70 of the of the present invention in which the adhesive layer is in the pattern of a plurality of substantially "pie shaped" sections 72 leaving airflow passages 74 therebetween.

FIG. 8 illustrates an embodiment 80 of the of the present invention in which the adhesive layer is in the pattern of a plurality of "pie shaped" sections smaller than the pie shaped sections 72 and leaving the air flow passages 84 therebetween.

FIG. 9 illustrates an embodiment 90 of the of the present invention in which the adhesive layer is in the pattern of a plurality of substantially parallel arcuate segments 92 leaving airflow passages 94 therebetween.

FIG. 10 illustrates an embodiment 100 of the of the present invention in which the adhesive layer is in the pattern of a plurality of chevron shaped sections 112 leaving airflow passages 114 therebetween.

FIG. 11 illustrates an embodiment 110 of the of the present invention in which the adhesive layer is in the pattern of a plurality of "dots" arranged in a regular pattern of two concentric circles leaving airflow passages 114 therebetween.

FIG. 12 illustrates an embodiment 120 of the of the present invention in which the adhesive layer is in the pattern of a plurality of randomly shaped segments 122 leaving airflow passages 124 therebetween.

FIG. 13 illustrates an embodiment 140 of the present invention in which the adhesive layer is in the form of small "✚" shaped segments 142 in a spaced apart linear rectilinear array defining the airflow passages 144 therebetween.

In each of the embodiments of the present invention, the cover is preferably fabricated from a vinyl or similar sheet suitable for the purpose and having a uniform thickness on the order of about 0.01 mil to 0.4 mil with a preferred thickness on the order of 0.1 mil to 0.4 mil. Any suitable adhesive may used as the adhesive layer applied to the vinyl sheet of the cover. The adhesive should be uniform in thickness and having a relative easy peel strength to allow easy removal from the stethoscope either for discarding after use or repositioning prior to use. The adhesive layer is selected to be as thin as possible so as not to interfere with the sound transmission of the stethoscope. Many adhesives are well known in the art for the purposes specified herein.

The covers of the present invention may be fabricated in individual units with a peel off protective paper or plastic layer on the adhesive or in some form of dispensing arrangement. FIG. 14 illustrates a convenient dispensing arrangement in which a role 130 of covers 12 are mounted on a pull away sheet such as a waxed paper 132 pressed against the adhesive layer on the cover 12. If desired, perforation lines 134 may be provided to allow separation of the individual covers 12 from the roll 130. The roll 130 may be contained in a dispenser shown at 136.

FIG. 15 illustrates a dispensing arrangement for the covers 12 in which a planar array of a plurality of covers 12, such as three covers 12, are mounted on a pull away sheet of, for example, waxed paper 132. Perforation lines 134 may be provided if desired.

This concludes the description of the preferred embodiments of the present invention. Those skilled in the art may find many variations of the structure of the invention and the following claims are intended to cover all such variations and modifications as falling within the true scope and spirit of the present invention.

What is claimed is:

1. An improved detachable cover for a stethoscope wherein the stethoscope has a head with a diaphragm therein and a rim surrounding the diaphragm, the detachable cover detachably mountable on at least the diaphragm of the stethoscope head and the cover comprising, in combination:

a thin flexible membrane-like body member having an upper surface, a lower surface and a peripheral edge, said peripheral edge having a predetermined geometrical configuration substantially matching the geometrical configuration of the stethoscope head;

a peelable adhesive layer on said lower surface of said body member, and said adhesive layer is disposed on said lower surface of said body member in a predetermined pattern, said predetermined pattern providing for a plurality of of separate adhesive segments in a preselected spaced apart array for detachably adhering to at least the diaphragm of the stethoscope head for the condition of the cover installed thereon, said separate adhesive segments defining airflow channel means extending between said segments and said airflow channel means providing air flow passageways from regions inside said peripheral edge to regions external said peripheral edge for substantially preventing the formation of air pockets or air bubbles between the cover and the diaphragm of the stethoscope head.

2. The arrangement defined in claim 1 wherein:

said body member has an annular border portion extending radially inwardly from said peripheral edge a first preselected distance, and said peripheral edge of said body member is positioned outwardly from the rim of the stethoscope head for the condition of the cover applied thereto.

3. The arrangement defined in claim 1 wherein:

said separate adhesive segments are small dots of adhesive and said predetermined pattern is a random pattern of said dots of adhesive.

4. The arrangement defined in claim 1 wherein:

said separate adhesive segments are small dots of adhesive and said predetermined pattern is a regular pattern of concentric circles of said adhesive segments.

5. The arrangement defined in claim 1 wherein:

said separate adhesive segments are a plurality of substantially parallel lines of adhesive and said predetermined pattern is a substantially parallel, space apart array of said lines of adhesive extending across said body member between opposite peripheral edge portions of said body member.

6. The arrangement defined in claim 1 wherein:

said adhesive segments are a plurality of pie shaped segments in a spaced apart array extending radially inwardly on said lower surface of said body member from said peripheral edge.

7. The arrangement defined in claim 1 wherein:

said adhesive segments are a plurality of arcuate shaped segments in a spaced apart array extending across said body member on said lower surface of said body member from between opposed peripheral edge portions.

8. The arrangement defined in claim 1 wherein:

said adhesive segments are a plurality of chevron shaped segments in a spaced apart array on said lower surface of said body member.

9. The arrangement defined in claim 1 wherein:

said adhesive segments are a plurality of irregularly shaped segments in a spaced apart array on said lower surface of said body member.

10. The arrangement defined in claim 1 wherein:

said adhesive segments are a plurality of spaced apart segments in the form of "✢" disposed on said lower surface of said cover in a rectilinear pattern.

11. The arrangement defined in claim 2 wherein:

said border portion is substantially free of said adhesive segments.

12. The arrangement defined in claim 1 wherein:

said airflow passages have a substantially linear passage from regions inside said peripheral edge to regions external said peripheral edge.

13. The arrangement defined in claim 2 wherein:

said border portion is partially covered with said adhesive segments.

14. The arrangement defined in claim 2 wherein:

said body member is a vinyl plastic sheet having a thickness on the order of 0.01 mil to 1.0 mil.

15. The arrangement defined in claim 12 wherein:

said body member has a thickness in the range of 0.1 mil to 0.4 mil.

* * * * *